US006238916B1

(12) United States Patent
El Halawani

(10) Patent No.: US 6,238,916 B1
(45) Date of Patent: May 29, 2001

(54) DNA ENCODING TURKEY HYPOTHALAMIC VASOACTIVE INTESTINAL PEPTIDE

(75) Inventor: Mohamed E. El Halawani, Shoreview, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 08/995,369

(22) Filed: Dec. 22, 1997

Related U.S. Application Data

(63) Continuation of application No. 08/437,612, filed on May 9, 1995, now abandoned, which is a continuation-in-part of application No. 08/287,668, filed on Aug. 9, 1994, now abandoned.

(51) Int. Cl.[7] ........................... C12N 15/16; C12N 15/63
(52) U.S. Cl. ...................................... 435/320.1; 536/23.51; 536/24.1; 536/24.31; 536/24.33
(58) Field of Search .................................. 536/23.1, 23.5, 536/23.51, 24.1, 24.3, 24.31, 24.33; 435/320.1

(56) References Cited

U.S. PATENT DOCUMENTS

| | | |
|---|---|---|
| 4,016,258 | 4/1977 | Said et al. . |
| 4,356,270 | 10/1982 | Itakura . |
| 4,737,487 | 4/1988 | Watts et al. . |
| 4,835,252 | 5/1989 | Musso et al. . |
| 4,866,039 | 9/1989 | Wootton et al. . |

OTHER PUBLICATIONS

Bodner, M., et al., "Coding Sequences for Vasoactive Intestinal Peptide and PHM–27 Peptide are Located on Two Adjacent Exons in the Human Genome", *Proc. Natl. Acad. Sci. USA*, 82, 3548, (1985).
Giladi, E., et al., "The Complete Structure of the Rat VIP Gene", *Mol. Brain Res.*, 7, 261, (1990).
Gozes, I., et al., "Biosynthesis and Regulation of Expression", *Annals New York Academy of Sciences*, 527, 77 (1988).
Gozes, I., et al., "Vasoactive Intestinal Peptide Gene: Putative Mechanism of Information Storage at the RNA Level", *J. of Neurochemistry*, 48, 1136 (1987).
Itoh, N., et al., "Human Preprovasoactive Intestinal Polupeptide Contains a Novel PHI–27–like Peptide, PHM–027", *Nature*, 304, 547, (1983).
Lamperti, E.D., et al., "Characterization of the Gene Messages for Vasoactive Intestinal Polypeptide (VIP) in Rat and Mouse", *Mol. Brain Res.*, 9, 217, (1991).

Mauro, L.J., "Effects of Reproductive Status, Ovariectomy, and Photoperiod on Vasoactive Intestinal Peptide in the Female Turkey Hypothalamus", *General and Comparative Endocrinology*, 87, 481, (1992).
McFarlin, D.R., "Gallus gallus PH–27 and Vasoactive Intestinal Peptide (VIP) mRNA, complete sequence", *EMBL/GenBank/DDJB Databases, Accession No.* GG09350, (May 1994).
McFarlin, D.R., et al., "Sequence of a cDNA Encoding Chicken Vasoactive Intestinal Peptide (VIP)", *Gene* 154, 211–213 (1995).
Nishizama, M., et al., "Nucleotide Sequence Divergence and Functional Constraint in VIP Precursor mRNA Evolution Between Human and Rat", *FEBS Letters*, 183, 55, (1985).
Opel, H., et al., "Stimulation of Prolactin Release in Turkeys by Vasoactive Intestinal Peptide (42688)", *Proc. of the Soc. for Exp. Biology and Medicine*, 187, 455, (1988).
Proudman, J.A., et al., "Turkey Prolactin: Validation of a Radioimmunoassay and Measurement of Changes Associated with Broodiness", *Biology of Reproduction*, 25, 573, (1981).
Tsukada, T., et al., "Structure of the Human Vasoactive Intestinal Polypeptide Gene", *DNA*, 4, 293, (1985).
Yamagami, T., et al., "Complete Nucleotide Sequence of Human Vasoactive Intestinal Peptide/PHM–27 Gene and Its Inducible Promoter", *Annals of the NY Acad. Sci.*, 527, 87, (1988).
You, S., et al., "Turkey Hypothalamic Preprovasoactive Intestinal Peptide Lacks Peptide Histidine Isoleucine (Phi)–Like Sequences", *Poster Presentation, Department of Animal Science, University of Minnesota, St. Paul, MN* (Aug. 10, 1994).
El Halawani, M.E., et al., "Increased Egg Production by Active Immunization Against Vasoactive Intestinal Peptide in the Turkey (Meleagris galloparo)", *Biol. Reproduction*, 52, 179–183, (1995).
Lamperti, E.D., et al., "Characterization of the Gene Messages for Vasoactive Intestinal Polypetide (VIP) in Rat and Mouse", *Mol. Brain Res.*, 9, 217, (1991).
Nilsson, A., "Structure of the Vasoactive Intestinal Octacosapeptide from Chicken Intestine the Amino Acid Sequence", *FEBS Letters*, vol. 60, No. 2, pp. 322–326, (Dec. 1975).

Primary Examiner—Gary L. Kunz
Assistant Examiner—Stephen Gucker
(74) Attorney, Agent, or Firm—Schwegman Lundberg Woessner & Kluth P.A.

(57) ABSTRACT

The present invention provides an isolated and purified DNA molecule comprising a single coding region encoding (a) a turkey vasoactive intestinal peptide (VIP); (b) a turkey prepro vasoactive intestinal peptide or (c) a biologically active subunit of (a) or (b).

14 Claims, 12 Drawing Sheets

FIG. 1

```
                                                    1
                                                    Met Glu His Arg Gly Thr Ser Pro Leu Leu Ala Leu
  1  CGACGGATTCGCGGCTCCGTGGCGGCC                    ATG GAG CAC CGC GGC ACC TCC CCG CTC CTC GCC CTC
                                                                                    10
        Ala Leu Ser Ala Leu Cys Trp Arg Ala Arg Ala Leu Pro Pro Arg Gly Ala Ala Phe
 67     GCC CTC AGC GCC CTC TGC TGG AGG GCG CGG CTG CCC CCG CGG GGC GCC TTC
                             20                                    30
        Pro Val Pro Arg Leu Gly Asn Arg Leu Pro Phe Asp Ala Ala Ser Glu Ser Asp Arg
127     CCT GTG CCG CGA CTG GGA AAC AGA CTG CCC TTT GAT GCA GCC AGT GAA TCT GAC CGC
                   40                                    50
        Ala His Gly Ser Leu Lys Ser Glu Ser Asp Ile Leu Gln Asn Thr Leu Pro Glu Asn Glu
187     GCC CAT GGG TCC CTA AAG TCT GAA TCA GAC ATT TTG CAG AAC ACA CTA CCT GAA AAT GAG
                       60                                    70
        Lys Phe Tyr Phe Asp Leu Ser Arg Ile Ile Asp Ser Ser Gln Asp Ser Pro Val Lys Arg
247     AAA TTC TAT TTT GAT TTG TCC AGA ATT ATT GAT AGC TCC CAG GAC AGT CCT GTC AAA CGC
                         80                                    90
        His Ser Asp Ala Val Phe Thr Asp Asn Tyr Ser Arg Phe Arg Lys Gln Met Ala Val Lys
307     CAC TCT GAT GCT GTC TTC ACT GAC AAT TAC AGC CGC TTT CGA AAG CAA ATG GCT GTG AAG
                         100                                   110
        Lys Tyr Leu Asn Ser Val Leu Thr Gly Lys Arg Ser Gln Glu Leu Asn Pro Ala Lys
367     AAA TAC TTA AAC TCA GTT TTA ACT GGA AAA CGA AGC CAG GAA GAG TTA AAT CCA GCC AAA
                         120                                   130
        Leu Arg Asp Glu Ala Glu Ile Leu Glu Pro Ser Phe Ser Glu Asn Tyr Asp Val Ser
427     CTT CGA GAT GAA GCA GAA ATT CTT GAA CCT TCC TTT TCA GAA AAC TAT GAT GTT TCT
                         140                                   150
        Val Asp Glu Leu Leu Ser His Leu Pro Leu Asp Leu END
487     GTA GAT GAA CTG CTG AGC CAC CTC CCA TTG GAC CTC TGA AGGACACCTAGAAAAACTCTTCAACAAG
                         160
553  AACAAGTATTTTTGAGTTCCACATAGTATTTCAAAGAGATGACTTTAGTCATCAAATCTGAACAAATATGTTGTGAAG
632  TGAAAGTTGTGATATATTATTCTTATGTAATAAAGTTGATATTTACATTGTAAATACTGTTCTAGAGTTCTCTACT
711  GAAAGCTGTACATATGGATGCCAGTAAACAAATGAGAAGTCTGTAAGTCCATATGCTGTAAATCCTTTACTTCAATAA
790  ATTCATTTGAAAATGAAAAAAA
```

DNA ENCODING TURKEY HYPOTHALAMIC VASOACTIVE INTESTINAL PEPTIDE

This application is a continuation of U.S. patent application Ser. No. 08/437,612, filed on May 9, 1995, now abandoned, which is a continuation-in-part of U.S. patent application Ser. No. 08/287,668, filed on Aug. 9, 1994.

BACKGROUND OF THE INVENTION

The avian hypothalamus exerts a principally stimulatory influence on prolactin (PRL) secretion. Several lines of evidence support vasoactive intestinal peptide (VIP) as the most important prolactin-releasing factor (PRF) in birds. One vasoactive intestinal octacosapeptide is produced naturally in chickens and may be referred to as chicken VIP or cVIP. This particular VIP has the amino acid chain of His-Ser-Asp-Ala-Val-Phe-Thr-Asp-Asn-Tyr-Ser-Arg-Phe-Arg-Lys-Gln-Met-Ala-Val-Lys-Lys-Tyr-Leu-Asn-Ser-Val-Leu-Thr. cVIP is cross-reactive with any bird of the Avian species, including turkeys and ducks. In other words, turkeys and ducks also recognize cVIP.

VIP meets many of the qualifications of a PRF. For example, VIP stimulates PRL release from the anterior pituitary in vitro, and the response is closely correlated to the reproductive state of the animal. VIP also stimulates PRL release in vivo in median eminence-deafferentated hens (see, Opel et al., *Proc. Soc. Exp. Biol. Med.*, 187, 455 (1988)). Also, L. J. Mauro et al., *Gen. Comp. Endoc.*, 87, 481 (1992) reported the presence of high VIP concentration in median eminence, particularly the external layer. The presence of high affinity VIP receptors on the anterior pituitary cells has also been reported.

Further evidence that VIP is a PRF is provided by recent findings that lesioning of VIP cell bodies in the infundibular nuclear complex (INF) eliminates PRL increases associated with the photo-induced reproductive cycle and suppresses elevated PRL associated with incubation behavior. Finally, immunoneutralization of turkeys with endogenous VIP reduced both circulating PRL and pituitary PRL mRNA, totally blocked the PRL release effected by electrical stimulation of the medial preoptic nucleus, and blocks the hormonal and behavioral characteristics of incubating hens.

For example, the active immunization of turkey hens with VIP conjugated to an adjuvant protein was found to increase egg production. Although the bio-mechanical mechanism is not fully understood, it is believed that the antibodies so produced complex the turkey hen's naturally produced VIP. This naturally produced VIP regulates the secretion of the hormone prolactin from the pituitary gland of the turkey hen. In turn, increased prolactin secretion causes broodiness in turkey hens. Broodiness, in turn, is one of the factors that may lead to poor egg production. Accordingly, egg production is enhanced by binding the turkey hen's naturally produced VIP with the natural antibodies generated by the turkey before the turkey's VIP can act upon the turkey's pituitary gland to increase prolactin secretion.

Because of the prominent role VIP plays in the regulation of PRL secretion, it is likely that the secretion of PRL is mediated through changes in VIP secretion and/or gene expression, which may vary between the hypothalamic and hyperolactenemic birds. Therefore, a need exists to isolate, identify and regulate the structural gene encoding turkey VIP.

SUMMARY OF THE INVENTION

The present invention provides an isolated and purified DNA molecule comprising a DNA segment encoding a turkey vasoactive intestinal peptide. The present invention also provides an isolated and purified DNA molecule consisting essentially of a DNA segment encoding (a) a turkey vasoactive intestinal peptide, (b) a turkey prepro vasoactive intestinal peptide or (c) a biologically active subunit of (a) or (b). Preferably, the present invention provides a DNA segment which consists essentially of (a) DNA of SEQ ID NO:2, (b) DNA of SEQ ID NO:7, or (c) DNA of SEQ ID NO:9.

An isolated and purified DNA molecule, such as a probe or a primer, of at least seven nucleotide bases which hybridizes to these DNA molecules under the stringency conditions of Example 2, is also provided by the invention. The present invention also provides a probe or a primer comprising at least seven nucleotide bases of any of the above-disclosed single-stranded DNA sequences detectably labeled or having a binding site for a detectable label. As disclosed below, such probes or primers are useful to detect, quantify and amplify complementary DNA strands in avian tissue samples.

Thus, the present invention provides an isolated and purified DNA molecule comprising DNA encoding mature turkey vasoactive intestinal peptide (VIP) (SEQ ID NO:1), said VIP having the formula: His Ser Asp Ala Val Phe Thr Asp Asn Tyr Ser Arg Phe Arg Lys Gln Met Ala Val Lys Lys Tyr Leu Asn Ser Val Leu Thr, or a biologically-active subunit thereof. Preferably, the DNA encoding the VIP of SEQ ID NO:1 consists of the nucleotide sequence of SEQ ID NO:2: CAC TCT GAT GCT GTC TTC ACT GAC AAT TAC AGC CGC TTT CGA AAG CAA ATG GCT GTG AAG AAA TAC TTA AAC TCA GTT TTA ACT, which is also depicted, along with the amino acid sequence of VIP, in FIG. 1.

Representative isolated and purified DNA molecules of the invention consist of: (a) the entire DNA molecule depicted in FIG. 1, (SEQ ID NO:7), as well as (b) a DNA molecule which encodes prepro VIP, or a biologically active subunit of mature VIP or prepro VIP. These DNA molecules are double-stranded or single-stranded, preferably, they are cDNA. For example, the native DNA molecule encoding turkey prepro VIP of SEQ ID NO:8 is depicted under amino acids residues 1–165, and is designated SEQ ID NO:7.

Also encompassed by the invention is an isolated and purified DNA molecule encoding mature turkey VIP which hybridizes to a DNA sequence complimentary to DNA of SEQ ID NO:5 under the high-stringency hybridization conditions disclosed herein below, or under conditions of greater stringency.

As used herein, the terms "isolated and purified" refer to in vitro isolation of a DNA molecule or peptide from its natural cellular environment, and from association with other coding regions of the avian genome, so that it can be sequenced, replicated and/or expressed.

Preferably, the isolated and purified DNA sequences of the invention comprise a single coding region, and are no more than about 500–900 base pairs in length. Thus, the present DNA molecules are those "consisting essentially of" or those consisting of DNA segments encoding VIP, pre-pro VIP or a biologically active subunit of either. Unexpectedly, certain DNA molecules of the invention were found to include a DNA segment encoding a peptide known as peptide histidine isoleucine (PHI), which is also within the scope of the term "turkey vasoactive intestinal peptide."

The term "biologically active" refers to a polypeptide which has at least about 50% of the in vivo biological activity of turkey VIP of SEQ ID NO:1, as determined by the assays disclosed in commonly-assigned U.S. Pat. No. 5,557,033 filed Sep. 22, 1992.

The present invention also provides an expression vector, preferably a linear vector, comprising an isolated DNA molecule encoding (a) turkey vasoactive intestinal peptide (VIP), said VIP having the formula of SEQ ID NO:1; (b) prepro VIP of SEQ ID NO:8; or (c) a biologically active subunit peptide of (a) or (b). Preferably, the vector comprises a single coding region, and comprises a second DNA sequence operably linked to the coding sequence, and capable of directing expression of the VIP polypeptide of (a)–(c), such as a promoter region operably linked to the 5' end of the coding DNA sequence. Such expression vectors can be constructed and employed to transform host cells, i.e., procaryotic cells, in order to produce preselected VIP peptides. Although the present vectors contain only one VIP coding region, they also can contain a DNA sequence which is a selectable marker gene or reporter gene, as described below. The expression vectors can also be constructed and employed to transform eukaryotic cells. The present invention also provides a transformed eukaryotic host cell, which host cell contains an exogenous avian vasoactive intestinal peptide gene comprising: a native vasoactive intestinal peptide gene; and a DNA molecule encoding an exogenous avian vasoactive intestinal peptide wherein the DNA molecule expresses the exogenous avian vasoactive intestinal peptide gene at detectable levels.

The present invention also provides a method of introducing and expressing an exogenous avian vasoactive intestinal peptide gene into a host cell comprising: transforming host cells in vitro with an expression cassette comprising a DNA molecule encoding an avian vasoactive intestinal peptide gene operably linked to a promoter functional in the host cell; and identifying a transformed host cell which expresses the DNA molecule. This method also provides isolated recombinant avian vasoactive intestinal peptides, which are recovered as products of the transformed host cells, when the cells are cultured under appropriate conditions.

BRIEF DESCRIPTION OF THE FIGURES

FIG. 1. Composite of the nucleotide sequence of three different overlapping tVIP cDNA clones (SEQ ID NO:7) and their corresponding inferred amino acid sequence (SEQ ID NO:8). Nucleotide residues are numbered in the 5' to 3' direction and amino acid residues are numbered beginning with the initiator methionine of the signal polypeptide. Residues presented in bold type and underlined represent the 28 amino acid tVIP. Two potential polyadenylation signals (AATAAA) are underlined. The putative PHI location, based on the PHI location in mammalian species, is marked by a double arrow.

DETAILED DESCRIPTION OF THE INVENTION

Figure 2:
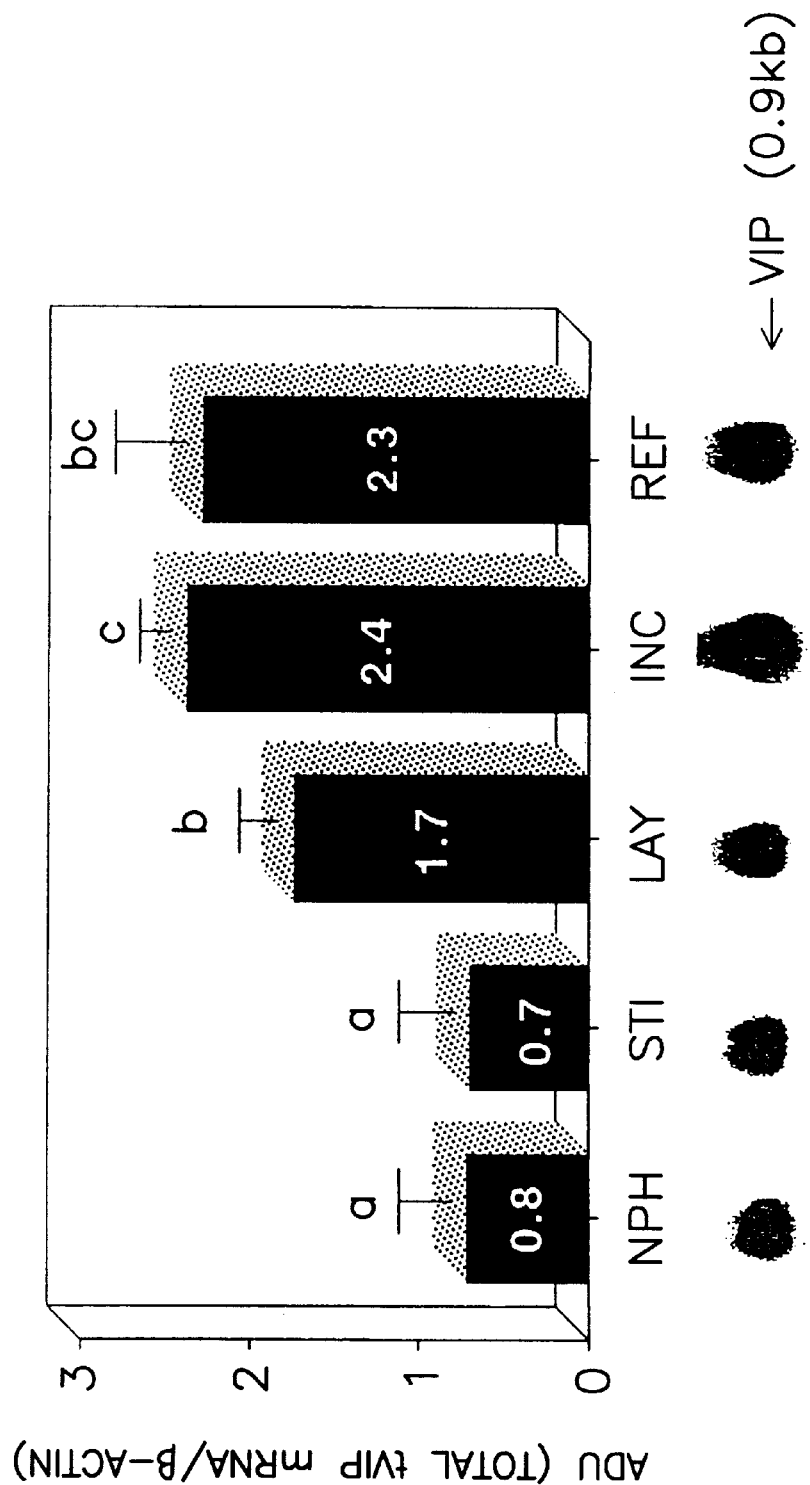
FIG. 2. Steady-state levels of hypothalamic tVIP mRNA during the reproductive cycle. Northern blots of turkey hypothalmic mRNA isolated during various portions of the reproductive cycle were first hybridized to a tVIP probe. Blots were then stripped and rehybridized with a chicken β-actin probe. The intensity of hybridization for tVIP and chicken β-actin mRNA was quantified and normalized. ADU=Arbitrary Densitometric Units. Values of 4 independent experiments with two replica are expressed as mean ±SE.$_{a,b,c}$ Means with different letters are statistically significant (P<0.05). A representative autoradiogram of a blot hybridized with a tVIP probe is shown below the schematic diagram. NPH=reproductively inactive. STI= photostimulated. LAY=laying. INC=incubation. REF= photorefractory.

Specifically, the present invention provides an isolated and purified cDNA molecule such as that represented by the complete nucleotide sequence shown in FIG. 1 (SEQ ID NO:7), which comprises a DNA sequence encoding prepro tVIP. The present invention further provides an isolated amino acid sequence consisting of the complete amino acid sequence shown in FIG. 1 (SEQ ID NO:8), as well as to an isolated and purified DNA molecule encoding mature VIP (SEQ ID NO:1, underlined in FIG. 1), such as that depicted in FIG. 1. The present invention also provides an isolated and purified DNA molecule encoding turkey mature VIP or preproVIP which hybridizes to a DNA sequence complementary to the DNA sequence of SEQ ID NO:5 under stringency conditions disclosed in Example 2. Polypeptides encoded by this DNA are also within the scope of the invention which exhibit at least 50% of the biological activity of turkey mature VIP, measured as discussed below.

The present invention also provides isolated and purified DNA molecules which provide "anti-sense" mRNA transcripts of the DNA sequences shown in FIG. 1. For example, one such DNA molecule comprises a sequence consisting of the base pairs TCAATTTTGACTCAAATTCATAAA- GAAGTGTCGGTAAACGAAAGCTTTC GCCGACAT- TAACAGTCACTTCTGTCGTAGTCTCAC (SEQ ID NO:5) or a functional subunit thereof, which when expressed from an expression vector in a host avian cell, will function to block the production of avian VIP by said cell.

The polymorphic cDNA sequences of the present invention can be introduced into the genome of cell lines, whether mammalian, bacterial, or insect cell lines, by in vitro techniques known in the art, to yield a transfected cell line having the cDNA stably integrated into its genome, so that the bioactive VIP molecules of the present invention are expressed by the cell lines. That is, the present invention also provides a transfected cell line having a genome augmented by a recombinant (non-native) DNA sequence, preferably by a chromosomally integrated recombinant (genetically engineered) DNA sequence that includes a gene for encoding turkey VIP, preproVIP or a bioactive subunit of either molecule.

As used herein, the term "cell line" is intended to refer to well-characterized homogenous, biologically pure populations of cells that are neoplastic or which have been "immortalized" in vitro by methods known in the art. The cell line is preferably of avian origin, but cell lines derived from other species may be employed, including murine, ovine, hamster, human, bovine, and the like or from prokaryotes or insects.

"Transfected" is used herein to include any cell or cell line, the genome of which has been altered or augmented by the presence of at least one recombinant DNA sequence, which DNA is also referred to in the art of genetic engineering as "heterologous DNA," "exogenous DNA," "genetically engineered," "non-native," or "foreign DNA," wherein said DNA was isolated and introduced into the genome of the cell or cell line by a process of genetic engineering. The cell lines of the present invention are typically produced by transfection with a DNA sequence in a plasmid expression vector, a viral expression vector, or as an isolated linear DNA sequence.

As used herein, the term "recombinant DNA" refers to DNA that has been derived or isolated from any appropriate tissue source, that may be subsequently chemically altered in vitro, and later introduced into host cells. An example of recombinant DNA "derived" from a source, would be a DNA sequence that is identified as a useful fragment within a given organism, and which is then chemically synthesized in essentially pure form. Another example of recombinant DNA "derived" from a source, would be a cDNA sequence that is prepared from isolated RNA. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering. Therefore, "recombinant DNA" includes completely synthetic DNA sequences, semi-synthetic DNA sequences, chimeric DNA sequences, DNA sequences isolated and purified from biological sources, and DNA sequences derived in vitro from RNA, as well as mixtures thereof. Generally, the recombinant DNA sequence is not originally resident in the genome which is the recipient of the DNA, or it is resident in the genome but is not expressed. As used herein, the term "chimeric" DNA sequence or molecule, refers to a DNA molecule comprising sequences derived from the genomes of two or more species that do not exchange DNA under normal conditions, or to DNA sequences which are linked in a manner that does not normally occur in the native genome.

The recombinant DNA sequence, used for transfection herein, may be circular or linear, double-stranded or single-stranded. Generally, the DNA sequence is in the form of chimeric DNA, such as plasmid DNA, that can also contain coding regions flanked by regulatory sequences which promote the expression of the recombinant DNA present in the progeny of the transfected host cell. For example, the recombinant DNA may itself comprise a promoter that is active in the host cells, or may utilize a promoter already present in the genome that is the transfection target.

The general methods for constructing recombinant DNA which can transfect target cells are well known to those skilled in the art, and the same conditions and methods of construction may be utilized to produce the DNA useful herein. For example, J. Sambrook et al., *Molecular Cloning: A Laboratory Manual,* Cold Spring Harbor Laboratory Press (2nd ed., 1989), provides suitable methods of construction.

Moreover, the general methods for isolating and purifying a recombinantly expressed protein from a host cell are well known to those in the art. Examples of the isolation and purification of such proteins are given in Sambrook et al.

Aside from recombinant DNA sequences that serve as transcription units for VIP or other portions thereof, a portion of the recombinant DNA may be untranscribed, serving a regulatory or a structural function. The recombinant DNA to be introduced into the cells further will generally contain either a selectable marker or a reporter gene or both to facilitate identification and selection of transfectants. Alternatively, the selectable marker may be carried on a separate piece of DNA and used in a co-transfection procedure. Both selectable markers and reporter genes may be flanked with appropriate regulatory sequences to enable expression in cells, particularly avian or mammalian cells. Useful selectable markers are well known in the art and include, for example, antibiotic and herbicide resistance genes. Preferred selectable markers for use in the transfection processes of the present invention include resistance to the antibiotic neomycin or hygromycin, or to herbicides such as glyphosate, phosphinothricin, and the like.

Reporter genes are used for identifying potentially transformed cells and for evaluating the functionality of regulatory sequences. Reporter genes that encode for easily assayable marker proteins are well known in the art. In general, a reporter gene is a gene that is not present in, or expressed by, the recipient organism or tissue and that encodes a protein whose expression is manifested by some easily detectable property, e.g., enzymatic activity. Preferred reporter genes for use in the transformation processes of the present invention include β-galactosidase, luciferase or chloramphenicol acetyltransferase.

Other elements such as introns, enhancers, polyadenylation sequences and the like, can also be part of the recombinant DNA sequence. Such elements may or may not be necessary for the function of the DNA, but may provide improved expression of the DNA by affecting transcription, stability of the mRNA, or the like. Such elements may be included in the DNA as desired to obtain the optimal performance of the transforming DNA in the cell.

Sources of nucleotide sequences useful in the present invention include PolyA$^+$ RNA from avian cells, from which the mRNA encoding the VIP can be derived and used for the synthesis of the corresponding cDNA by methods known in the art. Such sources include turkey hypothalami, for example.

The recombinant DNA can be readily introduced into the target cells by transfection with the expression vector comprising cDNA encoding the turkey VIP by the calcium phosphate procedure of C. Chen et al., *Mol. Cell Biol.*, 7, 2745 (1987). Transfection can also be accomplished by lipofection, using commercially available kits, e.g., provided by BRL, or electroporation.

The invention will be further described by reference to the following detailed examples.

EXAMPLE 1

VIP cDNA Isolation and Sequence Analysis

Nicholas Large White female turkeys were used throughout these studies. All birds were reared and housed in floor pens with trap nests. Feed and water were constantly available.

Total RNA was isolated from the hypothalami of incubating turkey hens using the cesium chloride-guanidinium isothiocyanate method (see, J. Sambrook et al., *Molecular Cloning: A Laboratory Manual*, Cold Spring Harbor Laboratory, New York (1989) at 7.19–7.29). Poly(A)$^+$ RNA was isolated by chromatography on oligo (dT) cellulose. A custom cDNA library was constructed by InVitrogen (San Diego, Calif.) in the phagemid vector pcDNAII. Positive colonies were isolated by colony screening on Colony/Plague Screen (Dupont, Boston, Mass.) using a murine VIP cDNA as described in Lamperti et al. (*Mol. Brain Res.*, 9, 217 (1991)). Only about 150 bp of the VIP coding region was labeled with [α-$^{32}$P] dATP, [α-$^{32}$P] dCTP, [α-$^{32}$P]dGTP and [α-$^{32}$P] TTP (Amersham Life Science, Arlington Heights, Ill.) using VIP-specific primers in a polymerase chain reaction (PCR).

The three largest putative clones (tVIP-1, -4, and -5) were selected for nucleotide sequence analysis. Both strands of each clone were sequenced using the dideoxy chain termination method with both the modified T7 polymerase (Sequenase; U.S. Biochemical, Cleveland, Ohio) and Taq DNA polymerase. Autoradiographs of sequencing gels were read manually or on a Applied Biosystems Model 373A (Microchemical Facility, University of Minnesota). The nucleotide and predicted amino acid sequences were compiled, analyzed, and compared with mammalian VIP cDNA sequences by using the homology search feature of the Intelligenetics Program.

FIG. 1 shows the complete nucleotide sequence of a composite sequence of the three different tVIP cDNA clones (SEQ. ID NO: 7). tVIP-1 and tVIP-5 were partial sequences beginning within the coding region at amino acid 30, whereas tVIP-4 included all of the 5' coding region plus an additional portion of 5' untranslated region (UTR). Otherwise, these three different clones were found to be identical when overlapping sequences were compared. The tVIP-4 clone contained 27 base pairs (bp) of the 5'-UTR, 495 bp of coding sequence, 282 bp of 3'-UTR and a 8 bp polyA track, while clones tVIP-1 and tVIP-5 lacked the 5' portion of the sequence.

Figure 4:
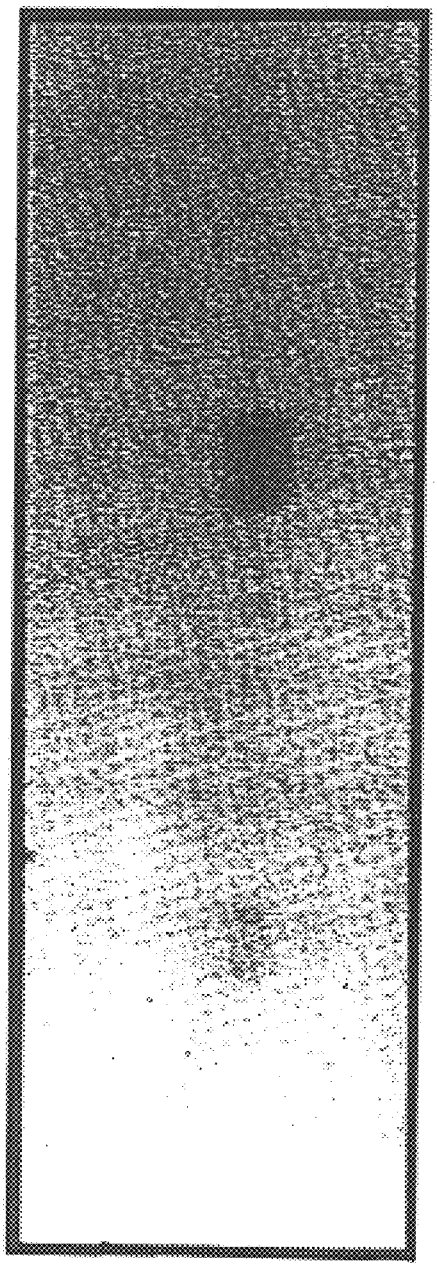
FIG. 4. Northern blot analysis of tissue-specific tVIP mRNA expression. Total cellular RNA was prepared from various turkey tissues. Twenty µg of total RNA was analyzed per lane with a tVIP probe. HYP=hypothalamus. ON=optic nerve.

The amino acid sequence (residues 94–121, bolded and underlined) deduced from nucleotide residues 307–390 showed high similarity to rat and human VIP (Nishizama et al., *FEBS Lett.*, 183, 55 (1985); Itoh et al., *Nature*, 304, 547 (1983)). As shown in FIG. 1, the 27 amino acid residue sequence of PHI-27 as well as the 8 additional amino acids flanking either side of PHI-27 in rat and human (Nishizama et al., *FEBS Lett.*, 183, 55 (1985); Itoh et al., *Nature*, 304, 547 (1983)) were not present in tVIP clones. Glycine together with the basic amino acids Lys and Arg form a carboxy-terminal amidation signal sequence (Bradbury et al., *Nature*, 298, 686 (1982)), which lies adjacent to the carboxy-terminus of VIP. The 3'-UTR of tVIP clones had two potential polyadenylation sites, AATAAA (FIG. 1, bolded and underlined, nucleotide residues 662–667 and 774–779). Northern blot analysis (FIGS. 2 and 4) revealed a processed tVIP transcript of approximately 900 bases which hybridized to the $^{32}$P-labeled tVIP cDNA probe.

EXAMPLE 2

Assay for Steady State Hypothalamic tVIP mRNA Abundance

Steady-state levels of hypothalamic tVIP mRNA were measured by Northern blot analysis using total cellular RNA isolated from turkeys at different reproductive stages (FIG. 2). The reproductive groups used were 1) reproductively inactive (nonphotostimulated) hens maintained under a 6L:18D lighting regime for at least 8 weeks, 2) photostimulated hens that had been switched from 6L:18D to 16L:8D lighting schedule for 10 days, 3) laying hens that were in the nest only once or twice a day and laid regularly, 4) incubating birds that were in the nest six times per day for at least two weeks and did not lay during that time but were allowed to remain in the nest, 5) incubating birds as in 4) but were nest deprived by transferring the hens to individual wire cages, 6) photorefractory hens that were maintained on a 16L:8D lighting schedule that had ceased nesting and egg laying and had completed molting. Blood samples were collected at various times. Upon sacrifice, the median eminence and hypothalamus were frozen in liquid nitrogen.

Total RNA was extracted from frozen tissues using guanidinium thiocyanate-phenol-chloroform method of P. Chomczynski et al. (*Anal. Biochem.*, 162, 156 (1987)). Total RNA was prepared for electrophoresis by the method of R. M. Forney et al. (*BRL Focus*, 10, 5 (1988)). Ten micrograms of total RNA was loaded per lane and fractionated on 1% agarose gels containing 2.2 M formaldehyde. RNA was transferred to Gene Screen membranes (Dupont, Boston, Mass.) by capillary action. The filter was prehybridized for 6 to 8 hours at 42° C. in a solution containing 50% formamide, 5×SSC (1×SSC=0.15M NaCl, 0.015M Na Citrate, pH 7.0), 1% SDS, 2× Denhardt's solution, and 25 μg/ml tRNA.

Blots were hybridized with the turkey VIP cDNA of FIG. 1 labeled by nick translation (with [α-$^{32}$P] dCTP (ICN, Irvine, Calif.)), according to the methodology of Sanger et al. (*Proc. Nat'l Acad. Sci.,* 74, 5463 (1977)). Hybridization and washing was conducted according to the manufacturer's directions under high stringency conditions. High stringency conditions are defined as hybridization of membranes at 42° C. for 16–18 hours in 50% formamide, 5×SSC, 1% SDS, 2× Denhardt's solution, 25 µg/ml tRNA, and washing once for 5 minutes in 2×SSC at room temperature (25° C.), once for 45 minutes in 2×SSC, 1% SDS at 52° C. and once for 45 minutes in 0.2×SSC, 1% SDS at 52° C. Membranes were air-dried and exposed to Kodak XAR-5 film with intensifying screens at −80° C. After autoradiography, the membranes were boiled for 30 min in 0.1×SSC plus 1% SDS or in 0.02×SSC plus 0.1% SDS at 70° C. for 1 hour to remove the VIP probe and then rehybridized with a nick translated chicken β-actin probe, using the methodology of Kost et al. (*NAR,* 11, 8287 (1983)). The preparation of these reagents is disclosed in *Cloning Manual,* cited hereinabove, or in the 1982 edition. Some of the reagents are available from Sigma Chemical Company (St. Louis, Mo.).

The band intensity of hybridizing VIP mRNA and β-actin transcripts was quantified from autoradiographs using a scanning densitometer (Model 4000, Ambis, Inc., San Diego, Calif.), and normalized to the band intensity of the β-actin mRNA band. Values were expressed as arbitrary densitometric units (ADU). The results are shown in FIG. 2.

Hypothalamic tVIP mRNA abundance was lowest in the reproductively inactive (NPH) and photostimulated (STI) hens but increased in laying (LAY) hens who exhibited 2.1- and 2.4-fold greater steady-state tVIP mRNA levels than the NPH and STI birds, respectively. The highest level of hypothalamic tVIP mRNA content was observed during the incubation (INC) stage (3.0-, 3.4- and 1.4-fold greater than NPH, STI and LAY, respectively). No significant difference in the steady-state tVIP mRNA levels, however, was observed between INC and photorefractory (REF) birds.

EXAMPLE 3

Median Eminence VIP Content and Serum Prolactin Levels

The ME content and serum prolactin levels during various stages of the reproductive cycle were analyzed. Serum prolactin concentrations were measured using a homologous radioimmunoassay (RIA) employing the methodology of J. A. Proudman et al. (*Biol. Reprod.,* 25, 573 (1981)). VIP was extracted from the median eminence with acetic acid and measured using a homologous radioimmunoassay, as disclosed by L. J. Mauro et al. (*Gen. Comp. Endoc.,* 87, 481 (1992)). The results are shown in FIG. 3, wherein the left bar of each pair of bars represents the PRL level (ng/ml) and the right bar represents the VIP level (ng/ml).

The ME VIP content (FIG. 3) increased gradually during the reproductive cycle, similar to that shown in the steady-state tVIP mRNA levels (FIG. 2) during reproductive cycles. VIP concentrations in the ME were lowest in the NPH and increased 1.4-fold in STI hens. An additional increase was seen in LAY hens who exhibited VIP concentrations 2.2-and 1.8-fold greater than NPH and STI birds, respectively. Highest VIP content in the ME was observed in INC hens (4.2-, 2.9- and 1.8-fold greater than NPH, STI, and LAY, respectively).

Figure 3:
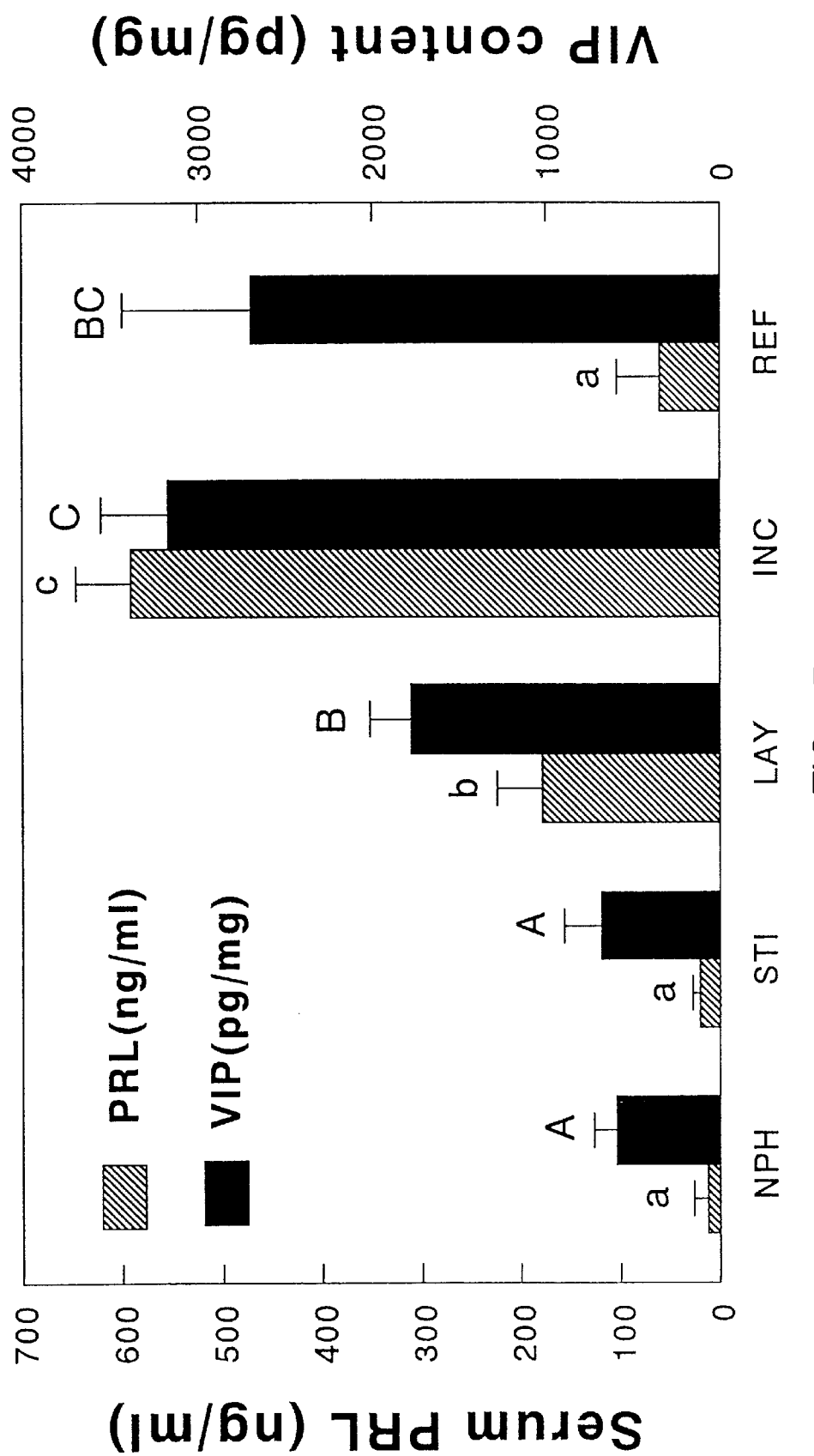
FIG. 3. Steady-state levels of ME VIP content (solid bar; pg/mg protein) and the associated serum PRL (cross hatched bar; ng/ml) during the reproductive cycle. Values of 4 independent experiments with two replica are expressed as mean ±SE.$_{a,b,c}$ Within experiments, means with different letters are statistically significant (P<0.05).

In some instances, the changes in hypothalamic VIP contents and levels of tVIP expression were correlated with elevated circulating PRL levels (FIG. 3). Increased ME VIP contents in STI hens (1.4-fold increase) were associated with higher serum PRL levels (2.1-fold increase) compared to those of NPH. Further increases in VIP contents in the ME (2.3- and 1.7-fold) and steady-state hypothalamic tVIP mRNA levels (2.1- and 2.4-fold) in LAY hens were associated with a higher serum PRL levels (24- and 12-fold increases) compared to those of NPH and STI hens, respectively. These increases in VIP expression were even higher in INC hens which correlated well with increased serum PRL levels (3.0-, 3.4-, and 1.4-fold increases in the steady-state hypothalamic tVIP mRNA levels; 4.2-, 2.9-, and 1.8-fold increases in the ME VIP contents; and 219-, 105-, 9-fold increases in the serum PRL levels compared to those of NPH, STI and LAY, respectively). While steady-state hypothalamic tVIP mRNA level remained constant and ME VIP content was slightly decreased (1.8-fold), a precipitous decrease in serum PRL level (42-fold) was seen in REF birds when compared to INC.

The data indicates that hypothalamic VIP concentrations and VIP mRNA contents were highest during the incubation phase of the reproductive cycle. Highest levels of serum PRL were also observed during this period.

EXAMPLE 4

Tissue Specific Levels of Turkey VIP mRNA Detected by RT-PCR

Initially, tissue-specific tVIP mRNA expression was analyzed by Northern blot analysis using total cellular RNA isolated from various turkey tissues. Only the hypothalamus and the optic nerve (FIG. 4) showed tVIP mRNA expression even though all tissues examined expressed β-actin mRNA. 15 Mammalian preproVIP (Nishizama et al., *FEBS Lett.,* 183, 55 (1985); Itoh et al., *Nature,* 304, 547 (1983)) transcripts have been shown to encode both peptide histidine isoleucine (PHI) and VIP peptides whereas the tVIP clones were found to contain only the VIP peptide (FIG. 1). To identify tissue-specific splicing patterns which might include the PHI sequence, a series of PCR analyses from reverse-transcribed RNA (FIGS. 5, 6 and 7) were performed.

Figure 5:
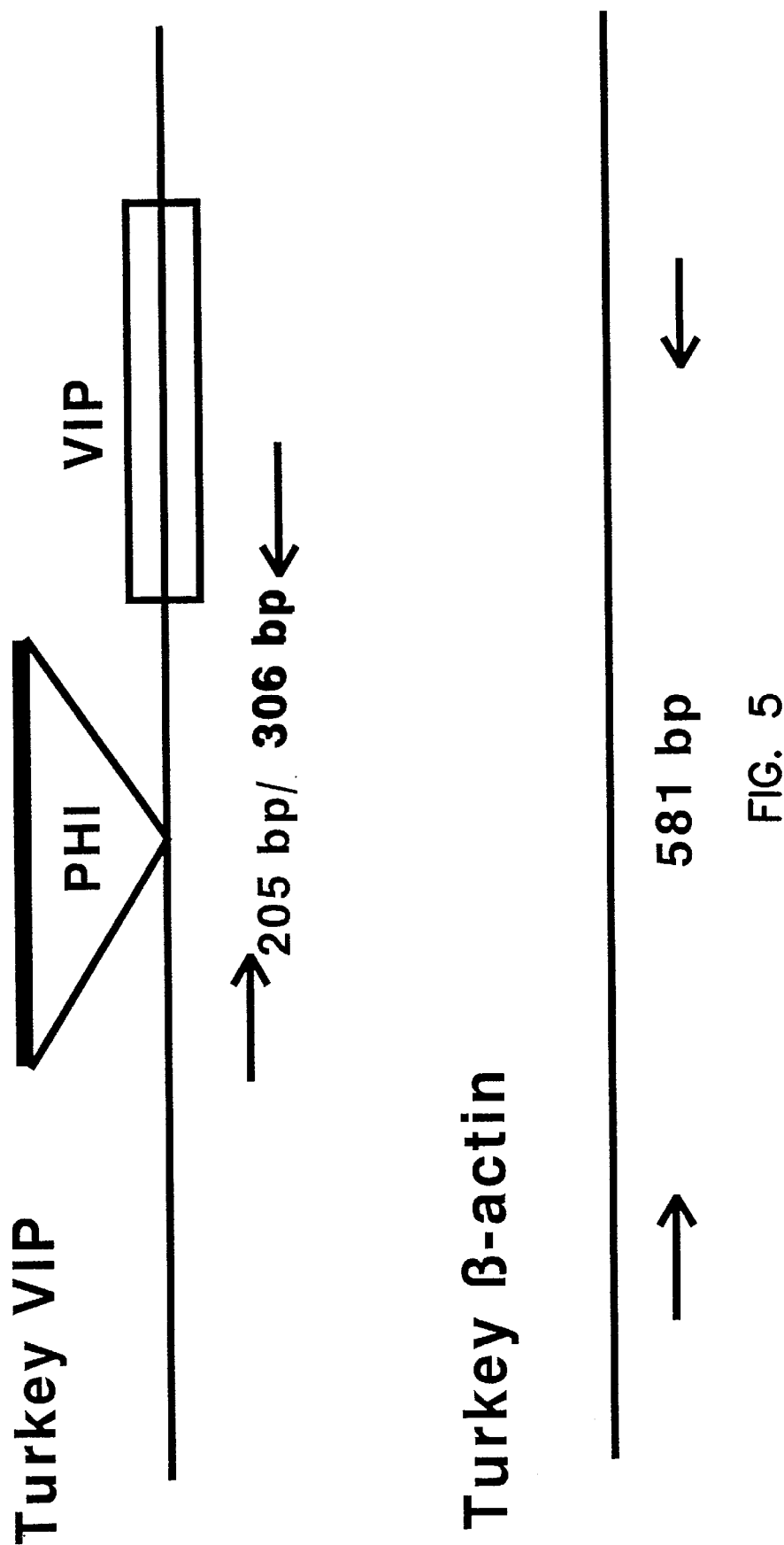
FIG. 5. Schematic representation of the position of synthetic oligonucleotide primers used for RT-PCR analysis. The tVIP-specific primer pairs were selected to specifically identify tVIP mRNAs that either lacked or contained (205 bp or 306 bp product, respectively) the PHI sequence. The β-actin specific primer pairs were selected to generate a 581 bp product as an internal control.

One µg of total cellular RNA from various tissues was reverse transcribed by Moloney murine leukemia virus reverse-transcriptase using oligo (dT) as a primer as recommended by Perkin Elmer Cetus (Norwalk, Conn.). Reaction mixtures (50 µl) were prepared using the Ampliwax hot start technique as recommended by the manufacturer (Perkin Elmer Cetus). The VIP- and β-actin-specific oligonucleotide primers used in the coamplification PCR reaction are: 1) VIP, a) 5'-TGAGGTTAAGTATTTCTTCACAGCCATTTGCTT (SEQ. ID NO: 11); b) 5'-GACCGCGCCCATGGGTCCCTAAAGTC (SEQ. ID NO: 12); 2) β-actin, a) 5'-ACCAGTAATTGGTACCGGCTCCTC (SEQ. ID NO: 13); b) 5'-TCTGGTGGTACCACAATGTACCCT (SEQ. ID NO: 14). The tVIP-specific primer pairs (SEQ. ID NO: 11 and 12) were selected to specifically identify tVIP mRNAs that were alternatively spliced and either lacked or contained the PHI sequence (either a 205 bp or 306 bp product, respectively). As an internal control for RT-PCR, β-actin-specific primer pairs (SEQ. ID NO:13 and 14) were employed (FIG. 5).

The amplification profile consisted of 30 cycles of 1 minute at 95° C., 1 minute at 65° C., and 1 minute at 72° C. The products of the reaction were analyzed by electrophoresis through 2% agarose and visualized by staining with ethidium bromide. After Southern blot analysis to verify VIP- and β-actin-specific amplification, the steady-state levels of VIP and β-actin mRNA by RT-PCR were quantified densitometerically by the band intensity of VIP and β-actin RT-PCR fragments and normalized to the band intensity of the β-actin.

Figure 6:
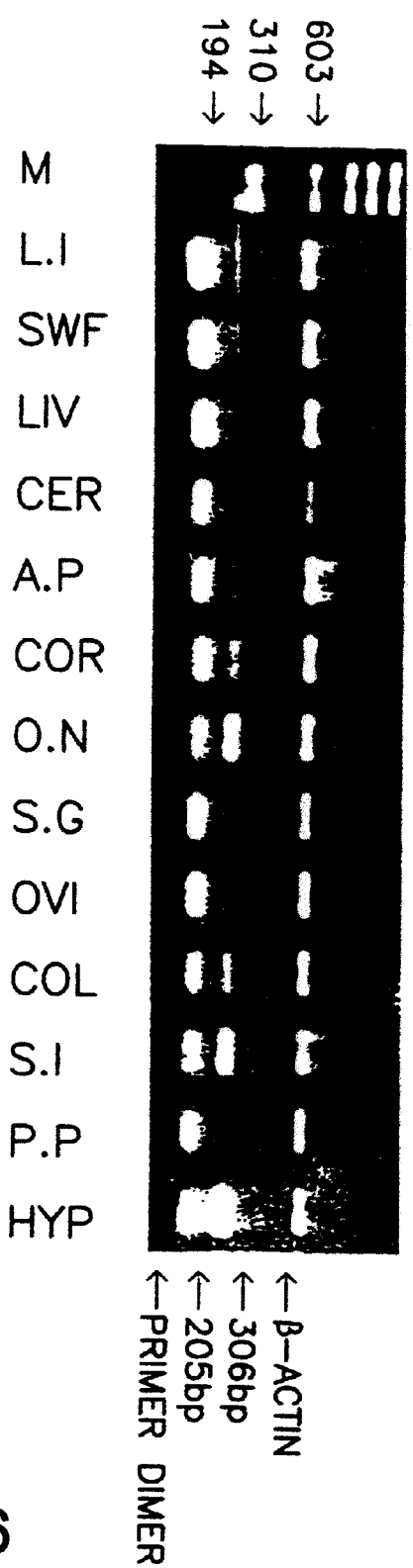
FIG. 6. RT-PCR analysis of the tissue-specific expression of alternatively spliced tVIP mRNAs. One µg of total RNA was reverse-transcribed into cDNA. tVIP- and β-actin-exon-specific primers were used to amplify tVIP- and β-actin-specific transcripts. Amplified DNA fragments were subjected to 2% agarose gel electrophoresis and then stained with ethidium bromide. Mobility of DNA size markers (in bp) and the expected mobilities of tVIP- and β-actin-specific amplified products are shown to the left and right, respectively.
Figure 7:
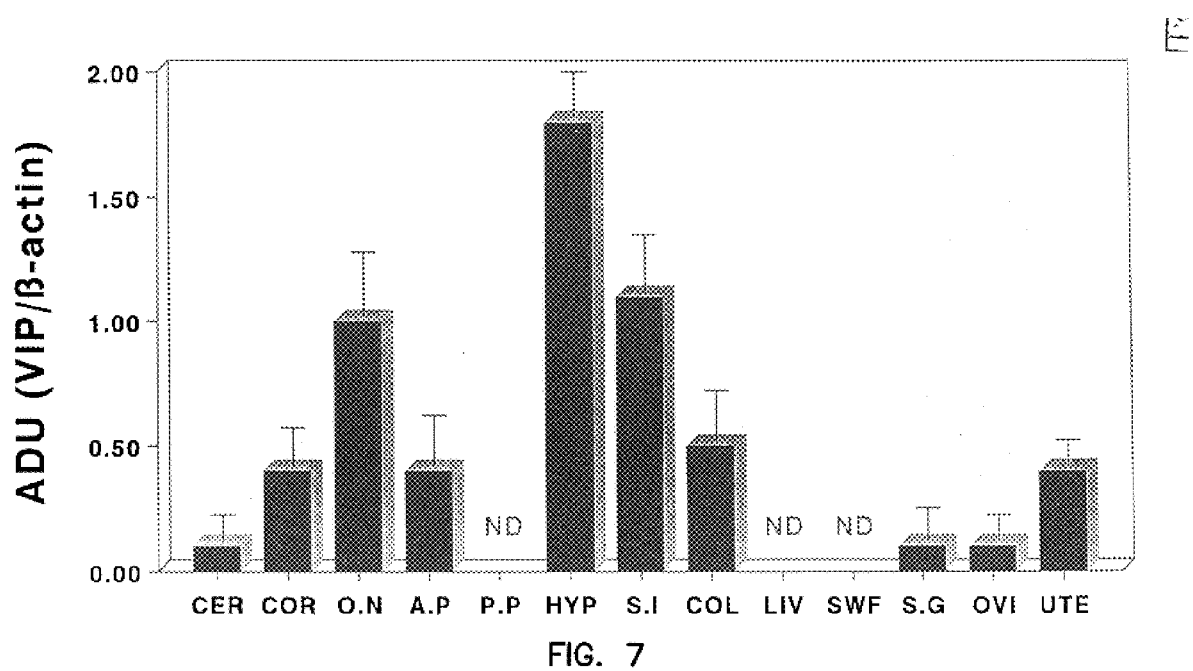
FIG. 7. Schematic representation of the relative levels of VIP mRNA in various turkey tissues as determined by RT-PCR analyses. The band intensity of amplified tVIP and β-actin fragments were quantified and normalized. Values of 4 independent experiments with two replica are expressed as mean ±SE. ND=non-detectable.

The tVIP mRNA expression was highest in the hypothalamus (1.8±0.18/ADU) followed by small intestine (1.1±0.23/ADU) and the optic nerve (1.0±0.26/ADU). Detectable levels were also observed in the cortex (COR), anterior pituitary (A.P.), colon (COL) and uterus (UTE). The cerebrum (CER), shell gland (S.G.) and oviduct (OVI) showed lower levels of tVIP mRNA expression (FIGS. 6 and 7).

Tissue-specific differential expression of transcripts that coded for either VIP or both VIP and PHI peptides were observed. One transcript that was observed in every tissue showed VIP expression but lacked PHI, while the other larger transcript (observed only in the hypothalamus) encoded both VIP and PHI peptides (FIG. 6). However, PHI-specific primer pairs did not produce a transcript that specifically encoded PHI but lacked VIP in any of the tissues examined in this study.

While alternatively spliced transcripts could not be detected by Northern blot analysis due to the small differences in the size of the transcripts, RT-PCR analysis was able to quantify alternatively spliced mRNAs. The PCR amplification rate of the two different products was tested for different cycling times and these values were analyzed, and normalized. The slope of the amplification rate curves of these two different products remained constant through 24 to 35 cycles with a similar amplification efficiency for the two tVIP transcripts and β-actin-specific fragments (no significant changes were observed among those values obtained from different cycling parameters). Therefore, the initial relative amounts of the different mRNAs in the sample should be identical to the numerical values as determined for the corresponding PCR products.

Figure 8:
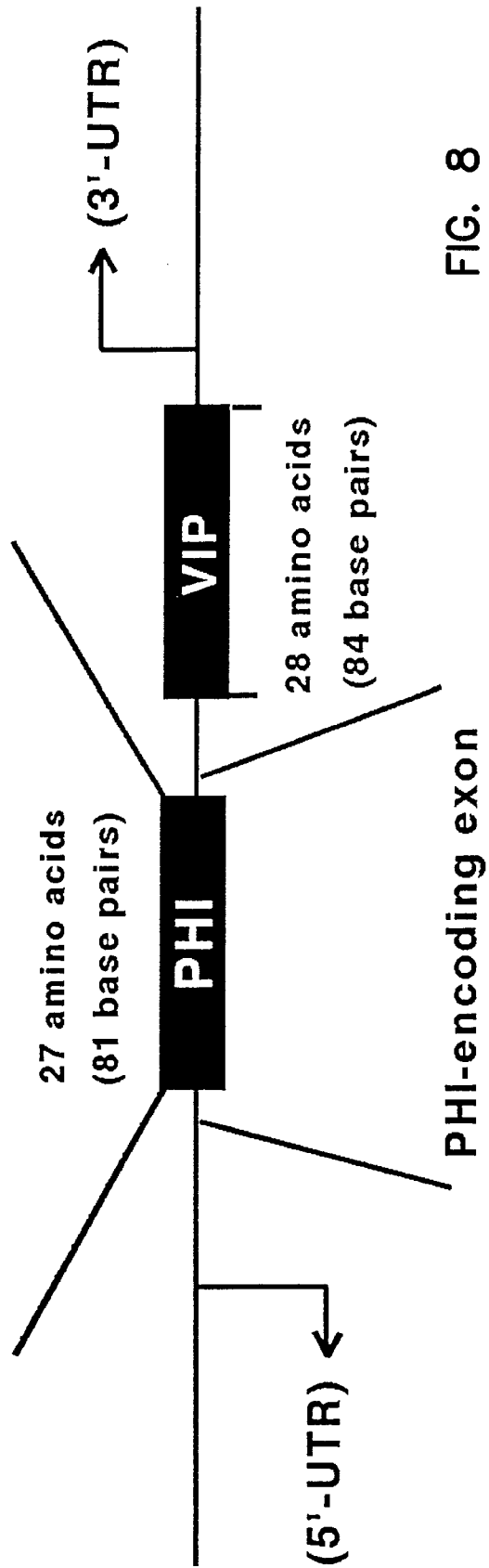
FIG. 8. Nucleotide sequence of the PHI-encoding exon (SEQ ID NO:9) and its corresponding inferred amino acid sequence (SEQ ID NO:10). Bolded and underlined letters represent the 27 amino acids of PHI peptide and shadowed letters represents nucleotide and amino acid sequences that flank either side of PHI.

The approximate 300 bp PCR fragment was isolated, purified and subsequently subcloned, followed by nucleotide sequence analysis. This fragment was identified as the alternatively spliced PHI containing sequence which encoded the 27 amino acid PHI peptide, as well as 4 amino acids that flanked both sides of PHI (FIG. 8). PCR amplification of turkey genomic DNA and partial sequence analysis showed the PHI encoding exon (105 bp) was flanked by introns on either side, with the VIP encoding exon located down stream of the PHI encoding exon. Thus, the turkey preproVIP gene encodes both VIP and PHI which are separated by at least one intron.

EXAMPLE 5

Figure 9:
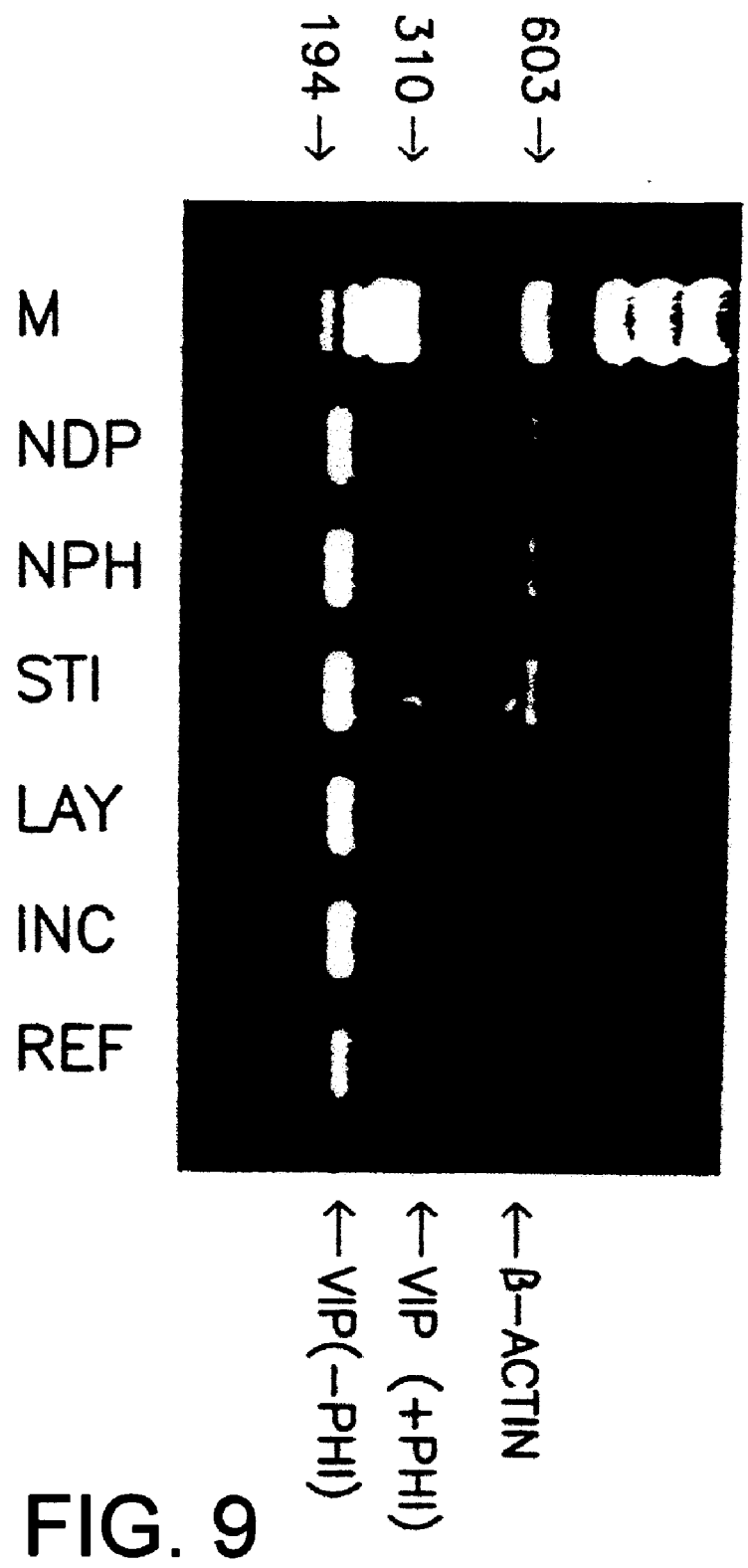
FIG. 9. RT-PCR detection of alternatively spliced preproVIP transcripts during various reproductive stages. One µg of total RNA was reverse-transcribed, amplified and analyzed. Mobility of DNA size markers are shown on the left. The expected mobilities of turkey VIP containing PHI or lacking PHI and β-actin-specific amplified products are shown to the right.
Figure 10:
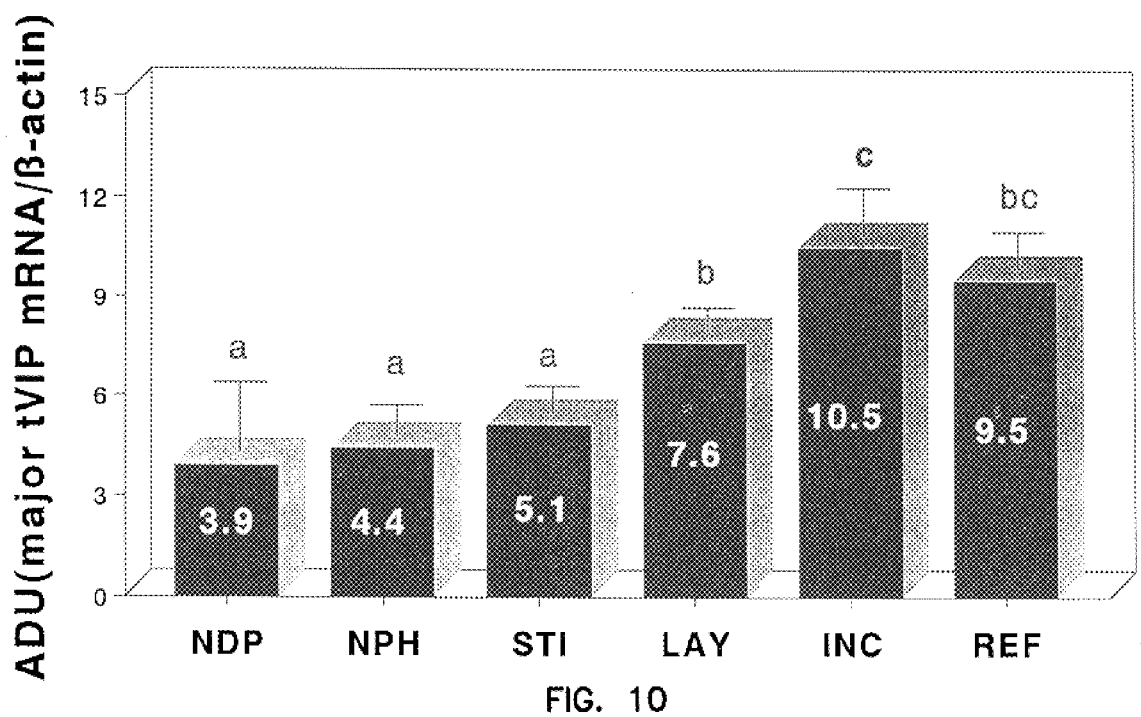
FIG. 10. Schematic representation of relative tVIP mRNA levels during various reproductive stages. The band intensity of amplified tVIP which does not contain PHI sequence was quantified and normalized. Values of 4 independent experiments with two replica are expressed as mean ±SE.$_{a,b,c}$ Within an experiment, means with different letters are statistically significant (P<0.05).

Quantification of Alternatively Spliced PreproVIP Transcripts during Various Reproductive Stages To determine if the alternatively spliced transcripts were equally expressed during various reproductive stages, levels of the major hypothalamic tVIP transcript were analyzed by RT-PCR (FIGS. 9 and 10). Low steady-state levels of the major hypothalamic tVIP mRNA were observed in NPH (4.4±0.9/ADU) and STI (5.1±0.8/ADU). A significant increase (1.7- and 1.5-fold) was seen in LAY hens (7.6±0.7/ADU) compared to the NPH and STI birds, respectively. Highest steady-state levels of major hypothalamic tVIP mRNA was observed in INC birds. However, no significant difference was seen between INC and REF hens (10.5±1.4/ADU and 9.5±1.1/ADU, respectively). Nest deprivation of INC, a procedure known to reduce circulating PRL, significantly decreased steady-state hypothalamic major tVIP mRNA content (NDP; 3.9±2.1/ADU, 2.7-fold decrease compared to INC hens).

Figure 11:
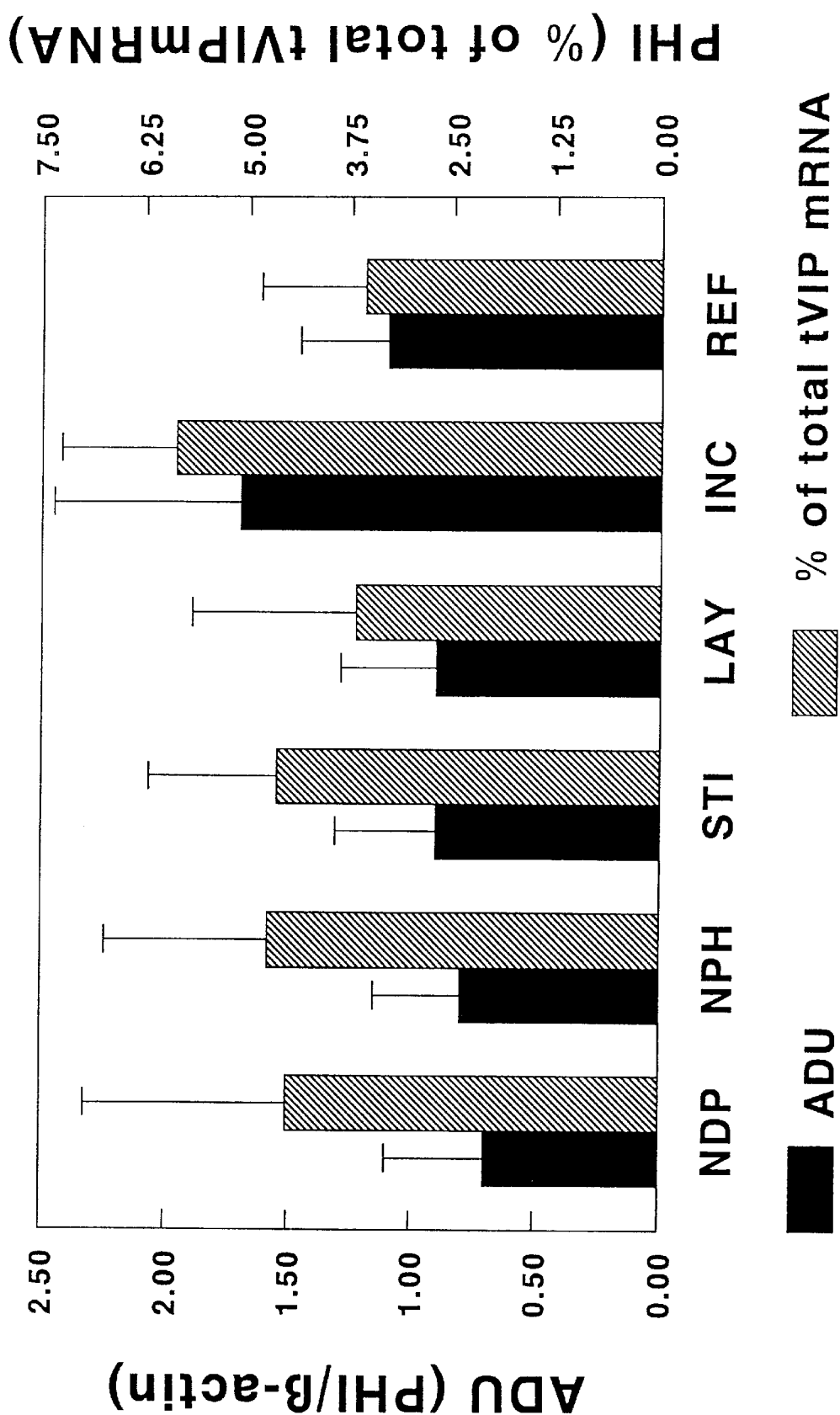
FIG. 11. Schematic representation of alternatively spliced minor tVIP transcripts during various reproductive stages. The band intensity of the amplified minor tVIP containing PHI sequence was quantified and normalized (solid bar). The minor tVIP transcript values were divided by total tVIP transcript values and represented as % of total tVIP mRNA (cross-hatched bar).
Figure 12:
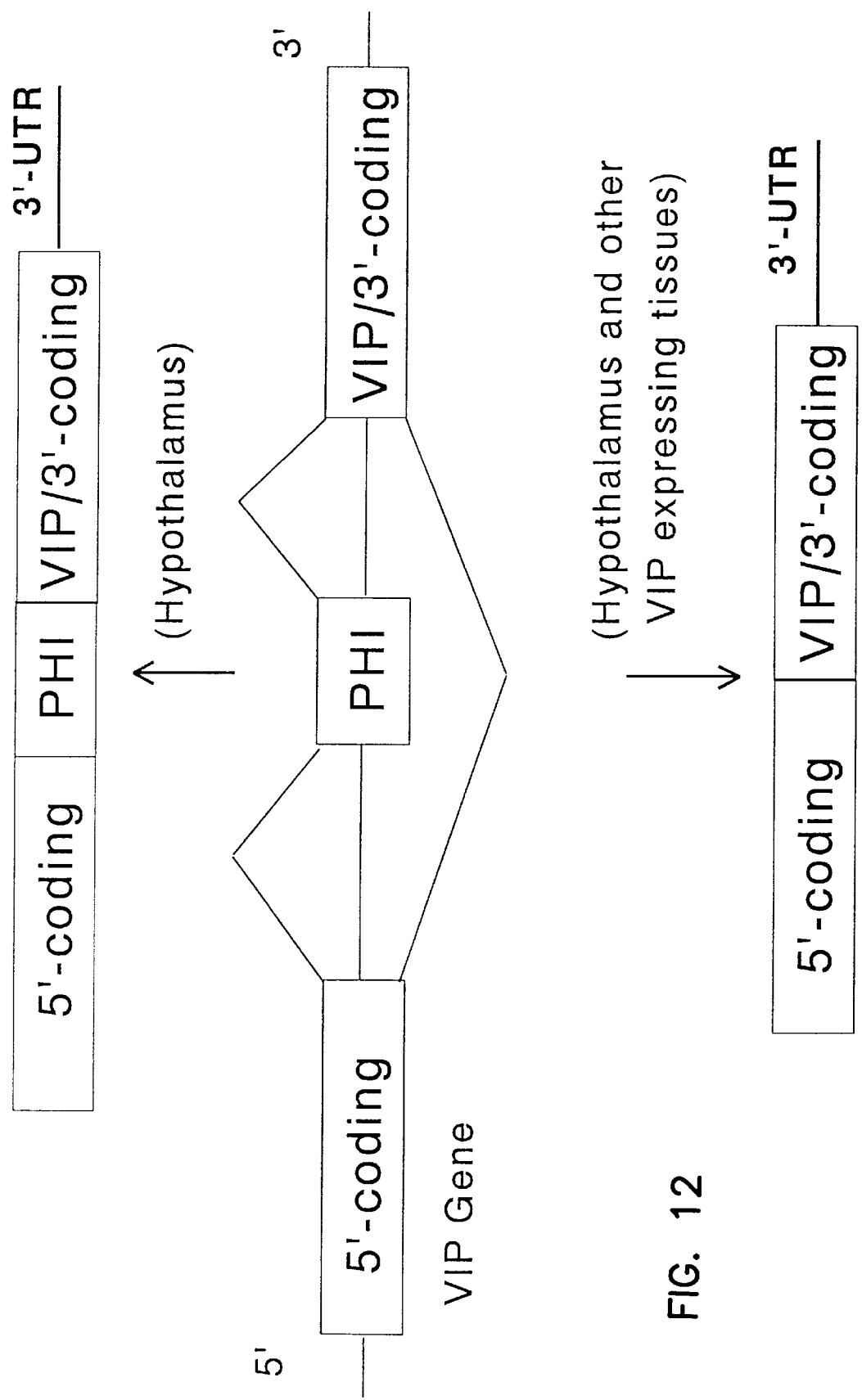
FIG. 12. Schematic representation of tissue specific alternative splicing pathways in the expression of the turkey preproVIP gene. In the structure of the VIP gene, boxes and lines correspond to exons and introns, respectively. Tissues in which only VIP is expressed or where both VIP and PHI are expressed are shown in parentheses.

Expressed levels of the minor hypothalamic tVIP mRNA transcript containing both PHI- and VIP-encoding exons were also analyzed by RT-PCR as described above (FIG. 11). In contrast to the gradual increase observed for the steady-state levels of the major hypothalamic tVIP mRNA during reproductive stages, neither the steady-state levels or relative amount of this transcript (as represented as percent of total tVIP mRNA) showed significant changes between reproductive stages.

DISCUSSION

The nucleotide sequence of the tVIP cDNA shares some nucleotide similarity to rat and human VIP cDNAs (Nishizama et al., *FEBS Lett.*, 183, 55 (1985); Itoh et al., *Nature*, 304, 547 (1983)). Nucleotides 25 through 31 of prepro tVIP (GCCATG; FIG. 1) conformed closely to the translation initiation consensus sequences (ACCATGG) described by Kozak (*Cell*, 44, 283 (1986)). Two potential polyadenylation signal sequences AATAAA were located 143 and 20 bases upstream from the poly A track.

Comparison of tVIP precursor molecule with the rat and human VIP precursor revealed that the processing sites for generation of VIP and PHI (or PHM) showed a high degree of similarity. This suggests that both turkey VIP and PHI are generated from their precursor by proteolytic processing, and that the peptides are carboxy-terminally amidated. The amino acid sequence similarity of tVIP to rat and human VIP is 69%. The 27 amino acids of turkey PHI, however, showed less sequence similarity (60%) compared to rat and human PHI.

Quantification of the steady-state hypothalamic tVIP mRNA and VIP content in the ME during a photo-induced reproductive cycle revealed a gradual increase in VIP gene expression, plateauing with highest levels in the INC and REF birds. The changes in VIP gene expression were associated with a coincident increase in circulating PRL. Thus, under conditions of hyperprolactinemia, hypothalamic VIP transcription is high. These results together with the finding that PRL transcription and pituitary PRL levels are greatest in lactotrophs from hyperprolactinemic incubating hens (Wong et al., *Biol. Reprod.*, 47, 598 (1992)) indicate that changes have occurred within the central VIPergic system as well as the pituitary of incubating hens to enhance PRL secretion. Furthermore, these findings suggest interactive regulatory mechanism(s) between both VIP and PRL gene expression. In this context, VIP elevates PRL mRNA levels in vivo (Talbot et al., *Endocrinol.*, 129, 496 (1991) Pitts et al., *Biol. Reprod.*, 50, 1344 (1994); Pitts et al., *Biol. Reprod.*, 50, 1350 (1994)) and in vitro (Xu et al., *Poultr. Sci.*, 71(5), 62 (1992)). Finally, it has been demonstrated that immunoneutralization of VIP reduced pituitary PRL content (Sharp et al., *J. Endocrinol.*, 122, 5 (1989)) and mRNA levels (Talbot et al., *Endocrinol.*, 129, 496 (1991)).

The incubation behavior-associated increase in PRL expression is maintained at high levels as long as nesting activity persists. Depriving incubating birds of access to nests lowers PRL levels (Mauro et al., *Endocrinol.* 125, 1795 (1989); Talbot et al., *Endocrinol.*, 129, 496 (1991)) and hypothalamic VIP-immunoreactivity (Mauro et al., *Endocrinol.*, 125, 1795 (1989)). These findings are consistent with the decline in hypothalamic VIP gene expression after nest-deprivation observed in the present study and indicates the importance of the nesting stimulus in maintaining elevated circulating PRL and hypothalamic VIP mRNA. The mechanism by which nesting activity modulates VIPergic gene expression remains an open question.

The elevated ME VIP content and steady-state tVIP mRNA levels combined with low circulating PRL levels were observed in the REF birds. This apparent discrepancy between VIP expression and PRL secretion could result from a decrease in pituitary responsiveness, since pituitary cells from REF birds exhibited the lowest VIP-induced PRL release (El Halawani et al., *Gen. Comp Endocrinol*, 80, 138 (1990)) and lowest pituitary VIP receptors (Rozenboim et al., *Biol. Reprod.*, 18, 1129 (1993)) when compared to laying and incubating birds. The non-photostimulated birds exhibited both low ME VIP content and steady-state tVIP mRNA levels indicating that there is a decline in VIP expression when photorefractory birds are transferred from a gonadal stimulatory lighting schedule of 16L:8D to a short day light regimen. The modulation of VIP gene expression by photic information is supported by the increase in hypothalamic VIP immunoreactivity following photostimulation (Mauro et al., *Endocrinol.*, 125, 1795 (1989); L. J. Mauro et al., *Gen. Comp. Endoc.*, 87, 481 (1992)). Further evidence is provided by the presence of opsin-like pigment in VIP neurons within the infundibular nuclear complex, a region thought to be the site of extraretinal hypothalamic photo-receptor (Silver et al., *Cell Tissue Res.*, 253, 189 (1988)). In the mammalian circadian oscillator, the suprachiasmatic nucleus (SCN), VIP positive neurons receive direct neural inputs from retinal ganglion cells (Ibata et al., *Neuro. Sci. Lett.*, 97, 1 (1989)). Manipulation of photic information, by optic tract transection or change in environmental lighting, can modify VIP gene expression within these ventrolateral SCN neurons (Albers et al., *Brain Research*, 437, 189 (1987); Stopa et al., *Mol. Brain Res.*, 4, 319 (1990)). The finding of this study lends support to a hypothetical scheme for VIP gene expression that is intimately linked to photoperiodic mechanisms active during reproduction. Such a model would seem appropriate in view of the fact that VIP is the most important PRF in birds and PRL is a hormone whose secretion is seasonally or photoperiodically dependent in many avian species (Nicholls et al., *Physiol. Rev.*, 68, 133 (1985)).

Although Mauro et al. (*Gen. Comp. Endoc.*, 87, 481 (1992)) demonstrated VIP immunoreactivity in several tissues, the data presented herein showed that only two tissues (optic nerve and hypothalamus) expressed VIP. In addition, the fact that none of the three different tVIP cDNA clones isolated contained the PHI-encoding exon suggests that the tVIP transcript could encode only one of the turkey neuropeptides, VIP. A highly sensitive and quantitative RT-PCR assay was developed to assess if potential alternative splicing patterns of tVIP transcripts occurred in a tissue-specific manner and to determine the variation of hypothalamic tVIP mRNA levels during various reproductive stages in the domestic female turkey. As was shown for a similar RT-PCR assay for detection of pit-1 mRNA isoforms (Day et al., *Mol. Endocrinol.*, 8, 374 (1994)), the relative amounts of individual mRNAs obtained by use of such a method are highly accurate and reproducible (Sandbrook et al., *J. Biol. Chem.*, 269, 1510 (1994); Goetzl et al., *J. Biol. Chem.*, 263 9083 (1988)).

The RT-PCR-amplified product of total RNA showed one band of the proper size for VIP lacking the PHI-encoding exon that was present in all tissues. A second amplified product found only in hypothalamic tissue was the correct size for VIP if it contained the PHI-encoding exon. The fragment was cloned and subjected to sequence analysis and found to correspond to the expected PHI portion of the preproVIP molecule.

The sequence encoding VIP and PHI are contained in two separate exons and the gene coding for VIP also codes for a VIP-related peptide PHI-27 (peptide-histidine-isoleucine amide) in rat or PHM-27 (peptide-histidine-methionine amide) in human. Such a tissue-specific alternative splicing mechanism of the preproVIP mRNA could give rise to polypeptide precursors containing only PHI or VIP, or both.

The arrangement of splice sites for the PHI and VIP exons would allow either exon sequence to be removed from a transcript without altering the reading frame of the remaining message. These exons would thus act as separate functional units, each encoding a separate neuropeptide complete with the peptide cleavage signals necessary to remove it from the precursor; one unit would be selectively removed from transcripts in a given tissue to cause tissue-specific expression of the other neuropeptide.

Using oligonucleotide and complimentary RNA probes, other investigators (Gozes et al., *Peptides*, 7(SI), 1 (1986); Gozes et al., *Ann. NY Acad. Sci.*, 527, 77 (1988); Goetzl et al., *J. Biol. Chem.*, 263, 9083 (1985); Gozes et al., *J. Cell. Biochem.*, 26, 21 (1984)) have described multiple VIP messages in mammalian tissues, which were considered to be either partially spliced or intact initial transcripts. One mRNA (from a human tumor) hybridized selectively to VIP-specific but not to PHI-specific oligonucleotides. However, a tissue-specific alternative splicing mechanism to produce a transcript encoding only one of the neuropeptides (PHI or VIP) was not found in the mammalian preproVIP gene. In mammals, there is no conclusive evidence for differential splicing to produce messages selectively expressing either PHI or VIP but rather the mature preproVIP mRNA contains both VIP and PHI coding sequences.

PHI and VIP have similar actions on a variety of potential target tissues (Tatemoto, *Peptides*, 5, 151 (1984)). PHI has been shown to be as potent as VIP in stimulating the release of PRL from dispersed rat anterior pituitary cells as well as from hemipituitaries (Werner et al., *Neuroendo.*, 37, 476 (1983); Samson et al., *Peptides*, 4, 817 (1983); Kaji et al., *LifeSci.*, 35, 641 (1984); Ohta et al., *Peptides*, 6, 709 (1989)). Although immunoreactive PHI and VIP are found in the same tissues, the relative levels of the two neuropeptides seem to vary substantially among different tissues (Christofides et al., *Peptides*, 5, 261 (1984)).

Radioimmunoassays have indicated that PHI and VIP concentrations are not equimolar in many mammalian tissues; VIP is significantly more abundant in certain parts of the gut, notably the stomach, and in the nasal mucosa and urogenital system (Christofides et al., *Peptides*, 5, 261 (1984)). These quantitative differences appear to be due to tissue-specific variations in post-translational processing (Yiangou et al., *Gastroentrol.*, 89 516 (1985); Yiangou et al., *BBRC*, 139, 1142 (1986); Yiangou et al.,*J. Biol. Chem.*, 262, 14010 (1987); Fahrenkrig et al., *Regul Peptides*, 12, 21 (1985)). Such regional variations in post-translational processing have been demonstrated for proopiomelanocortin in the pituitary and for proenkephalin in the hypothalamus and adrenal medulla (Douglas et al.,*Ann. Rev. Biochem.*, 53, 665 (1984)). However, the differential splicing of tVIP transcripts in a tissue-specific fashion demonstrated in this study may provide an additional explanation for the quantitative differences in tissue concentrations of PHI and VIP.

The levels of alternatively spliced tVIP transcripts containing both the PHI- and VIP-encoding exons did not significantly change between reproductive stages. These levels were maintained at approximately 4–6% of the total tVIP transcripts. These results strongly support the view that VIP is the predominant PRF in the adult turkey. Even though the minor PHI-VIP transcript exists at very low steady-state levels (and PHI peptide and PRL levels appears to be uncorrelated), the possibility still exists that the minor tVIP transcript might have physiological relevance if it were selectively induced by some factor or if its stability or translational efficiency differed from the major tVIP transcript which lacks the PHI-encoding exon. Also, it will be of interest to clarify its role, if any, in PRL regulation.

Based on the sequence similarity between the avian and mammalian PHI sequence, the cloning of the tVIP cDNA permits the study of the action and physiological role of PHI in birds. The role of PHI can be complemented by VIP during developmental stages and replaced by VIP in a tissue-specific manner. Revealing the tissue-distribution of VIP gene expression and tissue-specific alternative splicing contributes to an understanding of the physiological functions of the products of two alternatively spliced tVIP mRNAs as well as their relative roles in PRL regulation.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. An isolated and purified turkey DNA segment comprising a DNA fragment that encodes a polypeptide, wherein the expression of the DNA segment in turkey hypothalamus yields a RNA molecule that encodes a polypeptide comprising SEQ ID NO:4 or a RNA molecule that encodes a polypeptide comprising SEQ ID NO:1 and SEQ ID NO:7, wherein the expression of said DNA segment in non-hypothalamic turkey cells yields a RNA molecule that encodes a polypeptide comprising SEQ ID NO:4, and wherein the DNA segment which encodes SEQ:ID NO:4 comprises SEQ ID NO:2.

2. An isolated and purified turkey DNA segment comprising a DNA fragment that encodes a polypeptide, wherein the expression of the DNA segment in turkey hypothalamus yields a RNA molecule that encodes a polypeptide comprising SEQ ID NO:4 or a RNA molecule that encodes a polypeptide comprising SEQ ID NO:1 and SEQ ID NO:7, wherein the expression of said DNA segment in non-hypothalamic turkey cells yields a RNA molecule that encodes a polypeptide comprising SEQ ID NO:4.

3. An isolated and purified turkey DNA segment comprising a DNA fragment that encodes a polypeptide, wherein the expression of the DNA segment in turkey hypothalamus yields a RNA molecule that encodes a polypeptide comprising SEQ ID NO:4 or a RNA molecule that encodes a polypeptide comprising SEQ ID NO: 1 and SEQ ID NO:7, wherein the expression of said DNA segment in non-hypothalamic turkey cells yields a RNA molecule that encodes a polypeptide comprising SEQ ID NO:4, and wherein the DNA encoding SEQ ID NO:7 comprises SEQ ID NO:6.

4. An isolated and purified DNA segment comprising a DNA fragment encoding a polypeptide comprising SEQ ID NO:4.

5. An expression cassette comprising: the isolated DNA segment of claim 1, 2, 3 or 4 operably linked to a promoter functional in a host cell.

6. An isolated and purified DNA segment that is fully complementary to (a) SEQ ID NO:2, (b) SEQ ID NO:5 or c) SEQ ID NO:6.

7. The DNA segment of claim 1, 2, 3, 4 or 5 which is detectably labeled or binds to a detectable label and is employed as a hybridization probe.

8. An isolated and purified DNA segment consisting of SEQ ID NO:8.

9. An isolated and purified DNA segment consisting of SEQ ID NO:9.

10. The DNA segment of claim 8 or 9 which is employed as a primer.

11. An expression cassette comprising: a DNA segment which is fully complementary to (a) SEQ ID NO:2, (b) SEQ ID NO:5, or (c) SEQ ID NO:6, operably linked to a promoter functional in a host cell.

12. An expression cassette comprising: a DNA segment encoding turkey peptide histidine isoleucine, operably linked to a promoter functional in a host cell, wherein the DNA segment comprises SEQ ID NO:6.

13. An expression cassette comprising: a DNA segment encoding turkey peptide histidine isoleucine, operably linked to a promoter functional in a host cell, wherein the turkey peptide histidine isoleucine comprises SEQ ID NO:7.

14. An isolated and purified turkey DNA segment comprising a DNA fragment that encodes a polypeptide, wherein the expression of the DNA segment in turkey hypothalamus yields a RNA molecule that encodes turkey vasoactive intestinal peptide or a RNA molecule that encodes turkey vasoactive intestinal peptide and turkey peptide histidine isoleucine, wherein the expression of said DNA segment in non-hypothalamic turkey cells yields a RNA molecule that encodes a turkey vasoactive intestinal peptide, wherein the DNA segment comprises SEQ ID NO:2, and wherein the RNA molecule hybridizes at 42° C. in 50% formamide, 5× SSC, 1% SDS, and 2× Denhardt's solution to the complement of SEQ ID NO:5.

* * * * *

UNITED STATES PATENT AND TRADEMARK OFFICE
CERTIFICATE OF CORRECTION

PATENT NO. : 6,238,916 B1
DATED : May 29, 2001
INVENTOR(S) : El Halawani

It is certified that error appears in the above-identified patent and that said Letters Patent is hereby corrected as shown below:

<u>Column 10,</u>
Line 33, delete "15".
Line 33, start new paragraph beginning with the word "Mammalian".

<u>Column 22, claim 7,</u>
Line 29, delete "5" and insert -- 6 --, therefore.

Signed and Sealed this

Twenty-seventh Day of November, 2001

*Attest:*

NICHOLAS P. GODICI
*Attesting Officer* — *Acting Director of the United States Patent and Trademark Office*

SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
      (A) LENGTH: 28 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 1:

```
His Ser Asp Ala Val Phe Thr Asp Asn Tyr Ser Arg Phe Arg Lys Gln
1               5                   10                  15

Met Ala Val Lys Lys Tyr Leu Asn Ser Val Leu Thr
            20                  25
```

(2) INFORMATION FOR SEQ ID NO: 2:

(i) SEQUENCE CHARACTERISTICS:
      (A) LENGTH: 84 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 2:

CACTCTGATG CTGTCTTCAC TGACAATTAC AGCCGCTTTC GAAAGCAAAT GGCTGTGAAG    60

AAATACTTAA ACTCAGTTTT AACT    84

(2) INFORMATION FOR SEQ ID NO: 3:

(i) SEQUENCE CHARACTERISTICS:
      (A) LENGTH: 84 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 3:

TCAATTTTGA CTCAAATTCA TAAAGAAGTG TCGGTAAACG AAAGCTTTCG CCGACATTAA    60

CAGTCACTTC TGTCGTAGTC TCAC    84

(2) INFORMATION FOR SEQ ID NO: 4:

(i) SEQUENCE CHARACTERISTICS:
        (A) LENGTH: 165 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 4:

```
Met Glu His Arg Gly Thr Ser Pro Leu Leu Leu Ala Leu Ala Leu Leu
 1               5                  10                  15

Ser Ala Leu Cys Trp Arg Ala Arg Ala Leu Pro Pro Arg Gly Ala Ala
             20                  25                  30

Phe Pro Ala Val Pro Arg Leu Gly Asn Arg Leu Pro Phe Asp Ala Ala
             35                  40                  45

Ser Glu Ser Asp Arg Ala His Gly Ser Leu Lys Ser Glu Ser Asp Ile
 50                      55                  60

Leu Gln Asn Thr Leu Pro Glu Asn Glu Lys Phe Tyr Phe Asp Leu Ser
65                  70                  75                  80

Arg Ile Ile Asp Ser Ser Gln Asp Ser Pro Val Lys Arg His Ser Asp
                 85                  90                  95

Ala Val Phe Thr Asp Asn Tyr Ser Arg Phe Arg Lys Gln Met Ala Val
                100                 105                 110

Lys Lys Tyr Leu Asn Ser Val Leu Thr Gly Lys Arg Ser Gln Glu Glu
             115                 120                 125

Leu Asn Pro Ala Lys Leu Arg Asp Glu Ala Glu Ile Leu Glu Pro Ser
         130                 135                 140

Phe Ser Glu Asn Tyr Asp Asp Val Ser Val Asp Glu Leu Leu Ser His
145                 150                 155                 160

Leu Pro Leu Asp Leu
                165
```

(2) INFORMATION FOR SEQ ID NO: 5:

(i) SEQUENCE CHARACTERISTICS:
        (A) LENGTH: 812 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

```
CGACGGATTC GCGGCTCCGT GGCGGCCATG GAGCACCGCG GCACCTCCCC GCTCCTCCTC      60

GCCCTCGCCC TCCTCAGCGC CCTCTGCTGG AGGGCGCGGG CGCTGCCCCC GCGGGGCGCC     120

GCCTTCCCTG CTGTGCCGCG ACTGGGAAAC AGACTGCCCT TTGATGCAGC CAGTGAATCT     180

GACCGCGCCC ATGGGTCCCT AAAGTCTGAA TCAGACATTT TGCAGAACAC ACTACCTGAA     240

AATGAGAAAT TCTATTTTGA TTTGTCCAGA ATTATTGATA GCTCCCAGGA CAGTCCTGTC     300

AAACGCCACT CTGATGCTGT CTTCACTGAC AATTACAGCC GCTTTCGAAA GCAAATGGCT     360

GTGAAGAAAT ACTTAAACTC AGTTTTAACT GGAAAACGAA GCCAGGAAGA GTTAAATCCA     420

GCCAAACTTG CAGATGAAGC AGAAATTCTT GAACCTTCCT TTTCAGAAAA CTATGATGAT     480

GTTTCTGTAG ATGAACTGCT GAGCCACCTC CCATTGGACC TCTGAAGGAC ACCTAGAAAA     540

CTCTTCAACA AGAACAAGTT ATTTTTGAGT TCCACATAGT ATTTCAAAGA GATGACTTTA     600
```

GTCATCAAAT CTGAACAAAT ATGTTGTGAA GTGAAAGTTG TGATATATTT ATTTCTTATG      660

TAATAAAAGT TGATATTTAC ATTGTAAATA CTGTTCTAGA GTTCTCTACT GAAAGCTGTA      720

CATATGGATG CCAGTTAAAC AAATGAGAAG TCTGTAAGTC CATATGCTGT AAATCCTTTA      780

CTTCAATAAA TTCATTTGAA AATGAAAAAA AA                                    812

(2) INFORMATION FOR SEQ ID NO: 6:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

AGAAATGCAA GGCATGCTGA TGGAATTTTC ACCACTGTAT ACAGCCATCT TTTGGCTAAA       60

CTCGCTGTGA AGAGATATCT GCATTCGCTT ATTAGAAAAA GAGTT                      105

(2) INFORMATION FOR SEQ ID NO: 7:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 7:

Arg Asn Ala Arg His Ala Asp Gly Ile Phe Thr Thr Val Tyr Ser His
    1               5                   10                  15

Leu Leu Ala Lys Leu Ala Val Lys Arg Tyr Leu His Ser Leu Ile Arg
                20                  25                  30

Lys Arg Val
            35

(2) INFORMATION FOR SEQ ID NO: 8:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

TGAGGTTAAG TATTTCTTCA CAGCCATTTG CTT                                    33

(2) INFORMATION FOR SEQ ID NO: 9:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

GACCGCGCCC ATGGGTCCCT AAAGTC                                            26

```
-continued (2) INFORMATION FOR SEQ ID NO: 10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

ACCAGTAATT GGTACCGGCT CCTC                                              24

(2) INFORMATION FOR SEQ ID NO: 11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

TCTGGTGGTA CCACAATGTA CCCT                                              24
```